(12) United States Patent
Terwee et al.

(10) Patent No.: US 6,598,606 B2
(45) Date of Patent: Jul. 29, 2003

(54) METHODS OF IMPLANTING AN INTRAOCULAR LENS

(75) Inventors: Thomas Henricus Marie Terwee, Roden (NL); Hendrick Albert Weeber, Groningen (NL); Patricia Ann Piers, Groningen (NL)

(73) Assignee: Pharmacia Groningen BV, Groningen (NL)

( * ) Notice: Subject to any disclaimer, the term of this patent is extended or adjusted under 35 U.S.C. 154(b) by 5 days.

(21) Appl. No.: 09/865,009

(22) Filed: May 24, 2001

(65) Prior Publication Data

US 2002/0035399 A1 Mar. 21, 2002

Related U.S. Application Data

(60) Provisional application No. 60/209,082, filed on Jun. 2, 2000.

(30) Foreign Application Priority Data

May 24, 2000 (SE) ................................................ 0001934

(51) Int. Cl.[7] ................................................ A61B 19/00
(52) U.S. Cl. ........................ 128/898; 623/6.56; 623/907
(58) Field of Search .............................. 623/6.11–6.13, 623/6.56, 6.59, 902, 907; 606/107; 128/898; 600/318–321, 356–360, 398–406

(56) References Cited

U.S. PATENT DOCUMENTS

| 4,542,542 A | 9/1985 | Wright |
| 4,573,998 A | 3/1986 | Mazzocco |
| 4,608,050 A | 8/1986 | Wright et al. |
| 4,685,921 A | * 8/1987 | Peyman ..................... 623/6.13 |
| 4,919,151 A | 4/1990 | Grubbs et al. |
| 4,950,289 A | * 8/1990 | Krasner ..................... 623/6.13 |
| 5,224,957 A | 7/1993 | Gasser et al. |
| 5,278,258 A | 1/1994 | Gerace et al. |
| 5,391,590 A | 2/1995 | Gerace et al. |
| 6,164,282 A | 12/2000 | Gwon et al. |

FOREIGN PATENT DOCUMENTS

| EP | 0414219 | 2/1991 |
| WO | WO 9947185 | 9/1999 |
| WO | WO 0022459 | 4/2000 |
| WO | WO 0022460 | 4/2000 |
| WO | WO 0044379 | 8/2000 |

OTHER PUBLICATIONS

Nishi et al, *Arch Ophthalmol.*, 115:507–510 (1997).
Hettlich et al, *German J. Ophthalmol.*, 1:346–349 (1992).
O'Donnell, Jr., et al, *J. Cataract Refract. Surg.*, 15:597–598 (1989).

* cited by examiner

*Primary Examiner*—David J. Isabella
*Assistant Examiner*—Urmi Chattopadhyay
(74) *Attorney, Agent, or Firm*—Dinsmore & Shohl LLP

(57) ABSTRACT

The vision of an eye having an impaired lens is stored with an artificial lens implant. The method involves replacing the lens by a polymerizable material injected into the emptied lens capsule and thereby providing a new lens implant with a predetermined refractive value, while admitting the possibility of controlling and adjusting the refractive value of the eye during the surgical process.

36 Claims, No Drawings

METHODS OF IMPLANTING AN INTRAOCULAR LENS

This application claims the benefit of Provisional Application No. 60/209,082, filed Jun. 2, 2000.

FIELD OF INVENTION

The present invention refers to a method of restoring vision of an eye having an impaired lens with an artificial lens implant. The method involves replacing the lens by a polymerizable material injected into the emptied lens capsule and thereby providing a new lens implant with a predetermined refractive value, while admitting the possibility of controlling and adjusting the refractive value of the eye during the surgical process.

BACKGROUND OF INVENTION

In the field of ophthalmic cataract surgery, wherein a defective natural lens is replaced with an artificial lens, there has been a development towards lenses and methods, which inflict less surgical trauma. For many years most of the IOLs were made of poly(methylmethacrylate) (PMMA), a material with good optical characteristics and compatibility with tissues in the eye. A disadvantage of PMMA, however, is that it is a very rigid material and a surgical incision must be made large enough, at least 5–6 mm, for the implantation of the lens. With improved devices for removal of the natural lens by phacoemulsification, requiring only a rather small incision, there was a need for lenses with deformable optics, as disclosed in the U.S. Pat. No. 4,573,998 (Mazzocco). There are presently several types of foldable intraocular lenses on the market which can be inserted through a considerably smaller incision of about 3 to 4 mm, for example made from specifically designed silicone materials.

Even with the mentioned types of improved implantable IOLs, now available on the market, there is still a desire to obtain a lens which admits the use of an even smaller incision and behaves like the natural lens in the eye, i.e. will be accommodating with a focal point regulated by action of the ciliary muscle in the eye. In order to allow for a really small incision it would be necessary to form the lens inside the eye from a solution which is injected into the capsular bag or into a balloon placed inside the bag by means of a standard injection needle.

IOLs formed from an injected solution of a silicone prepolymer, crosslinker and catalyst have already been suggested in U.S. Pat. Nos. 5,278,258 and 5,391,590 (Gerace et al). Generally low temperature curing at body temperature means a slow process and up to 12 hours may be needed to complete their setting and their slow setting may result in material leakage out of the capsular bag through the surgical incision. In order to overcome this problem, U.S. Pat. Nos. 4,542,542 and 4,608,050 (Wright et al) disclose such a silicon based injected system which is partially cured by heat in the vicinity of the injection hole of the capsular bag to accomplish a first sealing effect.

Alternatively to thermocured silicone systems, photopolymerizable lens materials have been suggested which are activated after injection into the capsular by light in the presence of a photoinitiator. In the articles by Hettlich et al in German J Ophthalmol (1992), Vol. 1, pages 342–5 and 346–349, there are disclosures of how to employ photopolymerization of a monomer system injected into the capsular bag of the eye. An example of such an injectable system is also described in EP 414219, in which the liquid composition comprises a difunctional acrylate and/or methacrylate ester and a photoinitiator capable of being polymerized by light of a wavelength range between 400–500 nm. Further, the International patent application PCT/EP99/04715 is directed to an injectable photocurable aqueous solution of pre-polymerized units which is capable of forming a lens implant with a suitable elasticity modulus after final a crosslinking process triggered by visible light. Even if suitable polymerizable systems are at hand for preparing injectable lenses, there is still a considerable problem to obtain control of the refractive outcome of the eye after implantation. Accordingly, Hettlich et al suggested that by filling the capsular bag to varying degrees, or alternatively influencing the anterior or posterior capsular curvature, refractive control eventually would become possible.

O Nishi et al in Arch. Ophthalmol., 1997, Vol. 115, 507–510 describe experiments with direct injection of silicone material into the emptied capsular bag in cadaver pig eyes with subsequent plugging of the capsule and molding of the silicone into a synthetic lens. By using this procedure, the ability of the capsular bag to mold the injected silicone was investigated. It was found that different values of accommodation amplitude could be accomplished dependent on if the implanted lens was molded with a zonal tension applied on the capsule compared to when said tension was abolished. Nishi et al suggested that when (if) the eye is atropinized postoperatively, the lens capsule will conform to its non-accommodated state, which should yield the optimal amplitude of accommodation according to the investigated lens refilling principle. In the experiments referred to by H J Hettlich in Accommodative Lens Refilling Principles and Experiments © 1996 Pharmacia & Upjohn Groningen, the difficulties in obtaining the expected 30D myopic eye after lens injection are acknowledged.

Although there has been a considerable progress in the development of materials and surgical techniques for injectable lenses, considerable efforts are still needed to control the refractive outcome of this type of lenses. In particular, selection methods of suitable materials and improved control of the lens forming process after refilling the capsule will be necessary to carefully predict the refractive outcome of the eye subjected to lens replacement.

DESCRIPTION OF THE INVENTION

It is an object of the present invention to provide for a method of restoring the vision of an eye having an impaired lens to a predetermined refractive value of the eye by introducing a polymerizable fluid in the capsular bag It is also an object of the present invention to provide for a method wherein the refraction of the eye with the injected lens material is controlled and compared with a predetermined refractive value of the eye and when necessary adjusted to comply with said predetermined value before finalizing the polymerization to the final lens implant.

It is a further object of the present invention to provide for a method of selecting suitable polymerizable fluid to be introduced into the capsular bag of the eye and subsequent polymerization into an intraocular lens.

It is a still further object of the invention to provide for a method, wherein the capsular bag of the eye filled with a polymerizable fluid can be affected so as to vary and control the refractive value of eye before polymerizing the fluid into the final lens implant.

According to a first aspect, the present invention relates to method of pre-selecting a polymerizable fluid to be introduced into the capsular bag and formed to an implanted replacement lens for an impaired natural lens. Typically, the natural lens to be replaced suffers from cataract formation, but also presbyopic lenses, i.e. lenses having completely or partially lost their capacity of accommodation, are also conceivable to be substitute within the context of the presently invented methods. The polymerizable fluid is capable of being formed into an intraocular lens by means of one or several polymerization reactions. The resulting lens is intended to provide the eye with a determined desired refractive outcome value estimated as optically suitable or ideal for the individual elected to undergo surgery. The pre-selection method comprises measuring of selected eye dimensions including corneal curvature (anterior or posterior curves or both), the axial length of the eye and the anterior chamber depth. The person skilled in this technology is knowledgeable of several measurement methods to obtain this information and thereby finding relevant information about the eye, including the refractive value of the cornea. From these values the shape and the volume of capsular bag is estimated and thereby it is possible to calculate the quantity and refractive index of the polymerizable fluid to be introduced in the capsular bag in order to obtain a refractive value that sufficiently complies with the desired refractive outcome value of the individual eye. Typically, such calculations comprise the determination of a lens model refractive value (the refractive value necessary for the lens to restore the vision) from the measured corneal refractive value and the desired refractive outcome value. By further estimating the shape and thereby the volume of the individual capsular bag together with lens model refractive value, a quantity of polymerizable fluid with a specific refractive index is determined. According to one embodiment of the method, a polymerizable fluid then is selected from a kit of polymerizable fluids with a range of different refractive indices. In practical terms, the surgeon can select the determined quantity of the fluid of the kit having a refractive index value, which is most compatible to the estimated value of the refractive outcome value. Alternatively, a polymerizable fluid having an identical refractive index value to what has been estimated can be ordered from a manufacturer. Preferably, such kits of polymerizable fluids will have a range of refractive indices varying from about 1.39 to about 1.6. As discussed in more detail below, several suitable polymerizable fluids are conceivable for the kit which comply with such requirements as being easy to inject with conventional equipment, having suitably high specific gravity and providing options to obtain suitably high refractive indices and yet obtaining desirable mechanical characteristic for intraocular lenses after polymerization, including sufficiently low modulus to obtain an implanted lens, that can undergo accommodation when influenced by the ciliary muscles of the eye. The kit can typically comprise a range of such fluids filled in multi-compartment containers, separately stored from agents necessary to bring about the polymerization. Advantageously, the multi-compartment containers are provided with means to establish fluid communication between the containers just prior to the administration into the capsular bag and with means, either to inject the fluid, or to operate on the container with a conventional injection device. Many such containers are known to the skilled person and will not be described herein in more detail.

The present invention also pertains to a method of restoring the vision of an eye by removing an impaired lens from the capsular bag and replacing said lens with a quantity of a polymerizable liquid with the purpose of forming an intraocular lens with a predetermined refractive outcome. The defective natural lens is preferably removed by state of the art surgical interventions including eye opening with a small incision (about 1 mm), capsulotomy with capsulorhexis (about 1 mm) and lensectomy (removal of the natural lens) for example with phacoemulsification. Optional measures taken after finalizing the lensectomy can include conventional methods to preserve the capsular integrity and preparing the capsule, such as cleaning and anti-PCO treatment. The procedures of surgically removing the impaired lens are not parts of the present invention and will accordingly not be discussed in detail hereinafter. The inventive method comprises the determination of a desired refractive outcome value suitable for the eye, which is performed according to standard optical procedures, which may have been performed at an earlier occasion than the remaining steps of the method. Frequently, the desired refractive outcome of the patient is an emmetropic eye. The method further comprises the steps of introducing the polymerizable solution into the capsular bag and thereafter determining the refractive value of the eye. This refractive value is then if necessary compared with the desired refractive outcome value. The refractive value of the eye with the polymerizable fluid introduced in the capsular bag is then adjusted to obtain a value that complies with said desired value of refraction. In this context complying values means that they at best completely coincide with an accuracy relevant to the applied measuring means, or that the values sufficiently conform to each other considering what is clinically applicable in the present case. Further in this context, adjusting the refractive value of the eye will mean that the lens system of the capsular bag and polymerizable solution is affected, so as to bring about a sufficient change in eye refraction, such that said requested compliance is obtained. It is to be understood that the comparison of the mentioned refractive values and the subsequent adjustment if necessary can be repeated one or several times in an iterative process, so as to approach sufficiently complying refractive values. In such a repetitive process, it is also to be understood that different measures to adjust the refraction can be considered in each adjusting procedure. As will be explained below, the present invention introduces several alternatives to provide such adjustments by affecting the mentioned provisional lens system and thereby obtaining refractive control of the eye during the formation of the intraocular lens. When sufficiently complying values are obtained, the formation of a lens implant from the polymerizable liquid is initiated by starting a polymerization reaction from the constituents of the fluid. As a part of the formation process, it also intended that the polymerization can be performed in one or several steps with intermediate control of the refraction of the eye and if necessary refraction adjustments can be made in accordance with what has been described above. The refractive values of the eye as performed in the method after introducing the polymerizable fluid in the capsular bag can be made with on-line refractometry, for example as outlined in Journ. Cataract. Refract. Surg., 1989, Vol. 15, pp. 597–8.

According to a preferred embodiment, the polymerizable solution is pre-selected in accordance with what has been described in the foregoing part. Alternatively, a polymerizable fluid can be directly selected on the basis of other criteria.

When conducting the method it is also preferable to direct a rinsing fluid into the anterior chamber of the eye. The rinsing fluid is conventionally employed during cataract surgery in the process of lensectomy by introducing a probe in the anterior chamber of the eye. As will be discussed later, the rinsing fluid can be employed in the refractive control of the eye during lens formation. In the present method, the rinsing fluid is a saline solution provided with a specific refractive index. It is preferable that the polymerizable fluid is introduced in the capsular bag by means of injection, suitably through the orifice already created in the wall during the removal of the impaired natural lens. For this purpose, it is a prerequisite that the polymerizable fluid has a sufficiently low viscosity so it can be efficiently injected through a standard cannula with an 18 Gauge needle or finer. Preferably, the polymerizable fluid has a viscosity below about 60000 cSt and more preferably, below about 8000 cSt.

According to one aspect of the invention, the polymerizable fluid comprises a polymerizable polysiloxane composition, suitably also comprising a crosslinking agent to participate in the polymerizing forming process, i.e. a crosslinking process. According to one alternative of this aspect, the polysiloxane composition further comprises a catalyst activated by heat to initiate the crosslinking process. In another alternative, the polysiloxane composition comprises a photoinitiator that suitably is activated by visible light, in particular blue light. A useful polysiloxane composition can be found in the International Patent Application PCT/EP99/07780 that describes silicone compositions adapted for being thermocured in the capsular bag with a suitable high density above 1.0 g/cm$^3$. The polymerization after injection such a composition can be initiated by raising the temperature of the rinsing fluid to a value necessary to activate the catalyst driven polymerization. Typically, such an increase in temperature can be from about 20 to about 40° C. Alternatively, it is conceivable to use the photocurable compositions designed for intraocular lens production directly in the capsular bag of the eye, as described in the International Patent Application PCT/EP99/04715. From the teachings of these documents, the skilled person can readily obtain a wide range of polymerizable polysiloxane compositions suitable for injection into the capsular bag, having a range of different refractive indices varying from about 1.39 up to 1.6, as is suitable for the above-mentioned kit for selecting an appropriate polymerizable fluid. Both these documents, which herewith are incorporated as references in their entirety, provide polysiloxanes designed for injection into the capsular bag which by a specific selection of substituents on the polysiloxane backbone enables suitable variation range in refractive index, while still retaining characteristics of sufficiently high density (preferably higher than about 1.0 g/cm$^3$) and excellent mechanical characteristics for lens production.

According to an alternative aspect, the polymerizable fluid comprises an aqueous composition of a hydrophilic polymer carrying sites for crosslinking, wherein said aqueous composition further comprises a crosslinker. Preferably, the formation of a lens implant is initiated by activating a photoinitiator by irradiation of a predetermined wavelength or range of wavelengths. Most suitable in the context of the present method is to select a photoinitiator activated by visible light, preferably blue light. Examples of such compositions are found in the International Patent Application published as WO 99/47185, wherein crosslinkable hydrophilic units of different polymers are disclosed.

As earlier mentioned, it is an important part of the inventive method to be able to control the refraction of the eye, by performing refraction adjustments of the system consisting of the capsular bag containing the polymerizable fluid.

According to one embodiment the refractive value of the eye is adjusted by changing the pressure exerted on the capsular bag. A pressure change will result in that shape of the capsular bag is altered and thereby the curvature of its refractive surfaces. Varying the pressure exerted on the capsular bag is preferably performed by altering the pressure of the rinsing fluid as introduced in the anterior chamber of the eye with probe in fluid connection with a supply container. Accordingly, the fluid pressure of the rinsing liquid can conveniently be controlled by heightening or lowering the supply container as correlated to scale of height and pressure (mm Hg). The flowing rinsing fluid can thereby directly be used to exert different and readily controllable pressures on the anterior side of the capsular bag and thereby model its overall shape and its refractive value.

According to another embodiment, the refractive value of the eye is adjusted by affecting the state of accommodation and thereby obtaining control of the shape of the capsular bag. In a more accommodated state, the capsular bag with the fluid lens material is more rounded, whereas a less accommodated state of the lens results in a more flattened shape of the capsular bag. The different states of accommodation are caused by stretching and relaxation of the capsular bag by zonulas as influenced by the contraction and relaxation of the ciliary muscles. Several alternatives are conceivable to affect the state of accommodation. One alternative is either local or systemic administration of drugs, which influence the state of the ciliary muscles, such as pilocarpine. Another alternative to affect the state of accommodation is to visually stimulate the fellow eye not elected to surgery. The inadvertent accommodation following in the eye subjected to surgical intervention can thereby used for refractive adjustment.

According to a further embodiment, the refractive value of the eye is adjusted by changing the pressure inside the capsular bag. Suitably, such an adjustment is accomplished by changing the volume of the polymerizable solution. The volume can be adjusted either by re-introducing or withdrawing fluid from the capsular bag. Preferably, this is performed by means of an injection device through the previous injection site. It is also conceivable to accomplish changes in the fluid volume by letting the fluid swell or shrink in a controlled manner. It is to be understood that the different embodiments of adjusting the refraction can be combined in various manners. When conducting the inventive method, the surgeon will have the possibility to employ one way of affecting the capsular shape, thereafter controlling the refractive value, and if necessary for complying with the predetermined value use another embodiment of adjusting the refraction.

When starting the formation of the lens implant, a polymerizing process is initiated in the capsular bag by physically affecting the polymerizing fluid which can be accomplished in different manners dependent on what polymerizable fluid system that has been selected in accordance with the earlier discussions. According to one embodiment of the invention the polymerization is initiated by the influence of heat. The heating of the fluid can be generated by different means, such as irradiating the capsule with infrared radiation or by increasing the temperature of the rinsing liquid, as earlier mentioned. According to a different embodiment, the polymerization process can be initiated substantially instantaneously by means of irradiation, preferably by means of exposing the eye to visible light, in particular to blue light.

The step of forming a lens implant can also involve a partial polymerization the polymerizable fluid, before final polymerization. In such case, refractive value can be controlled after finalizing a partial polymerization and compared with the predetermined value. If these values do not comply sufficiently, one or several of the mentioned adjustment steps can be performed until the refractive value of the eye agrees with the desired predetermined value. Indeed several partial polymerization processes are conceivable, each with a subsequent refraction control and optional adjustment. The partial polymerization preferably applies to a local polymerization of the fluid, even if selective partial polymerization into a homogenous semi-solid fluid is considered to be a part of this embodiment. The local polymerization can be accomplished by heating the capsular at a selected part, for example by directed infrared radiation. Alternatively, heated rinsing liquid can be directed to a region or site of the capsular bag for a time sufficient to complete a local polymerization process. For example, local polymerization can be employed to obtain a first sealing effect of the fluid filled capsular bag. For this purpose, a thin sealing shell-like solid part around the inner periphery of the capsular bag can be obtained by directing heated rinsing liquid for a suitable time around its outer periphery. A local polymerization around the opening or injection site can also be obtained, for example by polymerizing around the injection needle immediately after introducing the liquid into the capsular bag. By effectively sealing the capsular bag, it is possible to more safely conduct necessary adjustments without risking that the liquid leaks out of the injection site. Partial and local polymerization, as outlined above, can also be obtained by irradiation with suitable light, for example by focussing the light to the desired site. After conducting the step or steps of partial polymerization performing refraction control of the eye, the lens forming process is continued by a final polymerization. This final curing step will result in the permanent intraocular lens which now will provide the eye with refractive value complying with the predetermined value and a restored vision. It is obvious necessity that the refractive value of the eye shall be kept constant, i.e. the shape of the capsular bag, during this final polymerization or during the entire formation step if no partial polymerization is conducted.

The present invention obviously also provides for an advantageous method of controlling the refractive value of the eye during ophthalmic surgery when the natural lens is replaced in the capsular bag by a polymerizable fluid. The control is exerted by the mentioned alternatives to modify the shape of the capsular bag into which a polymerizable fluid has been introduced.

Consequently the present invention admits that the patient is provided with an intraocular lens with an accurately determined refractive value that can restore the vision to a predetermined value. This is a considerable advantage when compared to conventional surgery with stiff or foldable lenses no refractive adjustments can be performed once the lens is inserted into the capsular bag. In combination with the fact that the present invention permits a surgical intervention causing less trauma from large incisions in the eye, it is obvious that highly advantageous contributions to the art are provided.

DETAILED AND EXEMPLIFYING
DESCRIPTION OF THE INVENTION

The inventive methods directed to refilling the natural human lens capsule with a polymerizable fluid are directed to securing that the intended post-operative refraction is achieved. One way is to adjust the lens power during the operation. Another way is to predict the amount of fluid and the refractive index of the fluid pre-operatively, which guarantee a correct post-op refraction. Within the context of the present invention it also possible to combine both methods. In such a case, the appropriate volume and refractive index of the polymerizable fluid are determined prior to the surgical procedure, then during the operation, the refraction is further fine-tuned to the intended value. When the human lens is impaired, for instance by cataract or presbyopia, the impaired lens can be removed out of the lens capsule. Thereafter a polymerizable fluid can be injected into the capsule and polymerized. The new lens is molded by the capsule. The newly molded lens must have the correct lens power in order to give the patient the intended postoperative refraction. The lens power depends largely on the amount of injected fluid and the refractive index of the fluid. This means that the lens power can be controlled by these two parameters. Based on the predictions of the volume and refractive index for a specific patient, the surgeon can be provided a kit of materials at the operating table, from which he select the right one for the specific patient. In the following example, a method is described which predicts the volume and refractive index of the polymerizable fluid, based on measurements on the individual patients and combined with data for the average human eye.

EXAMPLE 1

The determination is based on the combination of two sets of data:
1. General data of the human eye, measured on a representative population
2. Measurements of the individual patient 1. General Data Lens Thickness The lens thickness is very much depending on age. Within an age group, the spread in lens thickness is very small. Shum, Ko, Ng and Lin (1993) measured the lens thickness of a group of 76 subjects of virtually the same age (s.d. 1.2 month). On an average lens thickness of 3.49 mm he found a standard deviation of 0.02 mm, which is 0.5%. The age relation of the lens thickness is best described by Koretz, Kaufman, Neider and Goeckner (1989), who found a relation of $$LT = 3.220 + 0.021 * A \qquad (1)$$

LT=lens thickness [mm]
A=age [y]
When using this relation, the actual input for the calculation is age, and not lens thickness.

Relation Between Anterior and Posterior Lens Radius

The actual lens radii of an individual patient may differ a lot, however there is always a certain relation between the two. Based on measurements on human cadaver eyes, Glasser & Campbell (1999) found the relation of:

$$Rp = -0.261 * Ra - 2.631 \qquad (2)$$

Rp=posterior radius [mm]
Ra=anterior radius [mm]

Relation Between Lens Equatorial Diameter and Lens Focal Length

The lens equatorial diameter is hidden behind the iris. It can not be measured with the equipment that is normally available in the ophthalmic practice. Therefor a reasonable estimate can be made, using the relation that was found by Glasser & Campbell (1999), based on measurements on human cadaver eyes:

$$LD = 0.0502 * FL + 5.288 \quad (3)$$

LD=lens equatorial diameter
FL=lens focal length

Relation Between the Natural Lens Focal Length and the Refilled Lens Focal Length The lens capsule and the lens do not need to have the same shape. As a result it is possible that after refilling the lens, the shape of the lens has changed. This was seen in calculations of lens refilling. This phenomenon also follows from the results of Glasser & Campbell (1999): For most lenses the focal length changes after decapsulation of the lens. However, this effect disappears at the age of 60 years, which corresponds to the age of full presbyopia. From this it can be concluded that the focal length of the refilled lens will be equal to the focal length of the original lens, provided that the refill material has the refractive index of natural lens material.

Measurements on the Individual Patient

Keratometer

With the keratometer, the corneal power is measured. This is currently a standard measurement in cataract surgery. Alternatively, the corneal curvature (radius) can be measured. The relation between corneal curvature and corneal power is:

$$K = 337.5/Rc \quad (4)$$

K=Corneal power [D]
Rc=Curvature radius of the cornea
A-Scan

With an A-scan, the axial dimensions of the eye can be measured. Also this is currently standard practice in cataract surgery. In general, it results in a measure of the anterior chamber depth and the total axial length of the eye.

Refraction and Refraction History

The refraction is measured by the optometrist. When the patient is currently blind, the refraction can not be measured. In such a case there are two alternatives:
1. The refraction history of the patients eye, during the period that the patient was not blind.
2. The refraction and/or the refraction history of the patient's fellow eye.

Calculation Scheme

1. Determination of the lens thickness, from the age of the patient
2. Determining the radii of the lens, based on the known optical surfaces and refraction of the eye.
3. Determining the focal length of the natural lens
4. Determining the lens equatorial diameter, based on the lens focal length
5. Determining the volume of the natural lens.
6. Based on the desired post-op refractive outcome, select the appropriate refractive index.

The volume to be used is equal to the volume of the natural lens. The refractive index of the material is adapted, so that the predetermined refractive outcome for the patient will be reached.

Patient Data

Age: 63 year

Results of the ophthalmic exam:

| Keratometer reading: | 43.7 Diopter |
|---|---|
| A-scan: Axial length | 23.35 mm |
| Anterior chamber depth | 3.25 mm |
| Historic refraction: | +2.5 Diopter spherical equivalent (stable). |

Accordingly, the calculations according to the calculation scheme is:
1. According equation (1), the lens thickness is 4.543 mm.
2. According equation (4), the cornea has a radius of 7.723 mm.

The length of the vitreous is the axial length, minus the anterior chamber depth and minus the lens thickness. So far the optical system is:

| Surface | Name | Radius | Thickness | Refractive index |
|---|---|---|---|---|
| 1 | Cornea | +7.723 | 3.25 | 1.3375 |
| 2 | Lens | Ra | 4.543 | 1.422 |
| 3 | Vitreous | Rp | 15.557 | 1.336 |
| 4 | Retina | — | — | — |

Since, according equation (2), Rp is a function of Ra, there is only one variable in this system. This variable can be solved, using the condition that it has to result in the known or historic refraction. Here a paraxial ray tracing procedure is used, adapted from the spreadsheet that is used to calculate A-constants for IOL's. This results in the lens radii:

(Refraction Rx=spectacle refraction. For modeling the eye, the spectacle is made of Crown glass (Agarwal's principles of Optics and Refraction), 2 mm thick, with it's anterior surface 14 mm in front of the cornea).

Ra=12.286 mm
Rp=−5.838

3. The focal length of the natural lens is determined by the dimensions and refractive index:

Ra=12.286 mm
Rp=−5.838 mm
Thickness=4.543
Refractive index=1.422
→Lens power (P), according the thick lens equation is 21.40 diopter and the focal length is 1336/P=62.425 mm.

4. Equatorial diameter, according equation (3) is 8.422 mm.
5. The volume of the lens, based on an ellipsoid, with the known thickness and equatorial diameter is 186.7 $mm^3$.
The volume of an ellipsoid is:

$$V = \frac{4}{3} * \pi * a^2 * b$$

With:

a=diameter/2 b=thickness/2

6. The refractive index can now be chosen for a specific post-operative refractive outcome. An index of 1.422 will result in the pre-op (historic) refraction of 2.5 diopter. The result of different refractive indices can be calculated by paraxial ray tracing, and results in the following table (Rx=post-op refraction):

| Rx | η |
|---|---|
| −3 | 1.457 |
| −2 | 1.451 |
| −1 | 1.445 |
| 0 | 1.439 |
| 1 | 1.432 |
| 2 | 1.426 |
| 2.5 | 1.422 |
| 3 | 1.418 |
| 4 | 1.411 |
| 5 | 1.403 |
| 6 | 1.395 |

References

Agarwal, L. P. (1998). Agarwal's Principles of Optics and Refraction (5 ed.). New Dehli: CBS Publishers & Distributers.

Glasser, A., & Campbell, M. C. W. (1999). Biometric, optical and physical changes in the isolated human crystalline lens with age in relation to presbyopia. Vision Research, 39(11), 1991–2015.

Koretz, J. F., Kaufman, P. L., Neider, M. W., & Goeckner, P. A. (1989). Accommodation and presbyopia in the human eye—aging of the anterior segment. Vision Res, 29(12), 1685–1692.

Shum, P. J., Ko, L. S., Ng, C. L., & Lin, S. L. (1993). A biometric study of ocular changes during accommodation (see comments). Am J Ophthalmol, 115 (1), 76–81.

What is claimed is:

1. A method of restoring the vision of an eye by removing an impaired lens from the capsular bag and replacing said lens with a quantity of a polymerizable fluid, comprising the consecutive steps of:
   (a) determining a desired refractive outcome value suitable for the eye;
   (b) introducing the polymerizable fluid into the capsular bag;
   (c) determining the refractive value of the eye;
   (d) comparing the refractive values of steps (a) and (c);
   (e) adjusting the refractive value of the eye to comply with the value obtained in step (a); and
   (f) forming a lens implant from the polymerizable fluid providing the eye substantially with the refractive value determined in step (a).

2. A method according to claim 1, wherein rinsing fluid is directed into the anterior chamber of the eye.

3. A method according to claim 1, wherein the polymerizable fluid is introduced into the capsular bag by means of injection.

4. A method according to claim 3, wherein the polymerizable fluid has a sufficiently low viscosity so as to be capable of being injected through a standard cannula with an 18 Gauge needle or finer.

5. A method according to claim 4, wherein the polymerizable fluid has a viscosity below about 60,000 cSt.

6. A method according to claim 1, wherein the polymerizable fluid comprises a polysiloxane composition.

7. A method according to claim 6, wherein said polysiloxane composition further comprises a crosslinking agent.

8. A method according to claim 6, wherein said polysiloxane composition further comprises a catalyst activated by heat.

9. A method according to claim 6, wherein said polysiloxane composition comprises a photoinitiator.

10. A method according to claim 9, wherein said photoinitiator is activated by visible light, preferably blue light.

11. A method according to claim 1, wherein said polymerizable fluid comprises an aqueous composition of a hydrophilic polymer carrying sites for crosslinking.

12. A method according to claim 11, wherein said aqueous composition comprises a crosslinker.

13. A method according to claim 12, wherein said aqueous composition comprises a photoinitiator activated by visible light.

14. A method according to claim 1, wherein the refractive value is adjusted by changing the pressure exerted on the capsular bag.

15. A method according to claim 1, wherein the refractive value is adjusted by affecting the state of accommodation of the eye.

16. A method according to claim 15, wherein the state of accommodation is affected by administering drugs influencing the ciliary muscle.

17. A method according to claim 15, wherein the state of accommodation is affected by visually stimulating the fellow eye.

18. A method according to claim 1, wherein the refractive value is adjusted by changing the pressure inside the capsular bag.

19. A method according to claim 18, wherein the pressure inside the capsular bag is changed by changing the volume of the polymerizable fluid.

20. A method according to claim 1, wherein the step of forming a lens implant comprises polymerization under the influence of heat.

21. A method according to claim 18, wherein the heat is provided by increasing the temperature of the rinsing fluid.

22. A method according to claim 20, wherein the heat is provided by directing infrared radiation to the capsular bag.

23. A method according to claim 1, wherein the step of forming a lens implant comprises polymerization initiated by irradiation.

24. A method according to claim 23, wherein the irradiation comprises visible light.

25. A method according to claim 23, wherein the irradiation comprises blue light.

26. A method according to claim 1, wherein the step of forming a lens implant comprises partially polymerizing the polymerizable fluid, before final polymerization.

27. A method according to claim 26, comprising conducting the partial polymerization and subsequently repeating steps (c) and (d), before optionally adjusting the refractive value to comply with the value obtained in step (a), before final polymerization.

28. A method according to claim 27, comprising directing heated rinsing liquid around the periphery of the capsular bag.

29. A method according to claim 27, comprising directing heated rinsing liquid to a site of the capsular bag to accomplish a sealing effect.

30. A method according to claim 27 comprising directing infrared radiation to the capsular bag.

31. A method according to claim 26, wherein the partial polymerization comprises locally polymerizing the polymerizable fluid by heat.

32. A method according to claim 31, wherein heated rinsing liquid is directed to a region of the capsular bag for a time sufficient to accomplish local polymerization.

33. A method according to claim 1, wherein the forming of the lens implant is conducted when the eye is in an unaccommodated state.

34. A method according to claim 1, wherein the polymerizable fluid is pre-selected by a method comprising the steps of:

(i) determining the desired refractive outcome value suitable for the eye;

(ii) measuring one or several eye dimensions selected from the group consisting of corneal curvature, axial length of the eye, and anterior chamber depth;

(iii) estimating the shape of the capsular bag; and (iv) calculating the quantity and the refractive index of the polymerizable fluid to be introduced in the capsular bag for obtaining a refractive value that sufficiently complies with the desired refractive outcome of (i).

35. A method according to claim 1, wherein rinsing fluid is directed into the anterior chamber of the eye, wherein the refractive value is adjusted by changing the pressure exerted on the capsular bag, and wherein the pressure exerted on the capsular bag is changed by changing the pressure of the rinsing liquid.

36. A method according to claim 9, wherein said photoinitiator is activated by blue light.

* * * * *

UNITED STATES PATENT AND TRADEMARK OFFICE
CERTIFICATE OF CORRECTION

PATENT NO. : 6,598,606 B2  Page 1 of 1
DATED : July 29, 2003
INVENTOR(S) : Thomas H. M. Terwee et al.

It is certified that error appears in the above-identified patent and that said Letters Patent is hereby corrected as shown below:

Title page,
Item [57], ABSTRACT,
Line 1, change "stored" to -- restored --.

Column 12,
Line 4, delete ", preferably blue light".
Line 28, change "fluid." to -- fluid introduced into the capsular bag. --
Line 30, change "polymerization" to -- polymerizing the polymerizable fluid --.
Line 32, change "claim 18," to -- claim 20, --.
Line 45, change "final polymerization." to -- finally polymerizing the polymerizable fluid. --.
Line 49, change "step (a), before" to -- step (a), and before --; and
Line 50, change "final polymerization." to -- finally polymerizing the polymerizable fluid. --.

Signed and Sealed this

Twentieth Day of January, 2004

JON W. DUDAS
*Acting Director of the United States Patent and Trademark Office*